United States Patent [19]

Yoneda et al.

[11] 4,380,644

[45] Apr. 19, 1983

[54] 2-OXOIMIDAZOLIDINE DERIVATIVES

[75] Inventors: Naoto Yoneda, Suita; Jyoji Kato, Yawata; Keizo Kinashi, Yao, all of Japan

[73] Assignee: Tanabe Siyaku Co., Ltd., Japan

[21] Appl. No.: 291,105

[22] Filed: Aug. 7, 1981

[30] Foreign Application Priority Data

Nov. 21, 1980 [JP] Japan ................... 55-164829

[51] Int. Cl.$^3$ ........................................... C07D 233/26
[52] U.S. Cl. ................... 548/321; 424/273 R
[58] Field of Search .............. 548/321; 424/273 R

[56] References Cited

U.S. PATENT DOCUMENTS 3,225,033 12/1965 Johnson et al. ............... 548/321 X

OTHER PUBLICATIONS

*Chemical Abstracts*, 95:25624f (1981) [Ger. Offen. 3,016,960, 11/13/80, Toda et al.].

Primary Examiner—Richard A. Schwartz
Attorney, Agent, or Firm—Jordan B. Bierman; Linda Bierman

[57] ABSTRACT

A 2-oxoimidazolidine derivative of the formula:

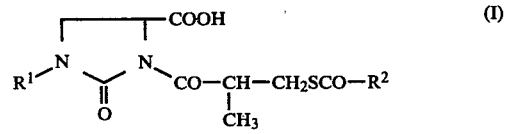

wherein $R^1$ is lower alkyl or phenyl-lower alkyl and $R^2$ is lower alkyl or phenyl, and a process for preparation thereof are disclosed. Said 2-oxoimidazolidine derivative (I) or a pharmaceutically acceptable salt thereof is useful as a hypotensive agent.

2 Claims, No Drawings

2-OXOIMIDAZOLIDINE DERIVATIVES

This Application claims priority under 35 USC §119 of Japanese Application 164829, filed Nov. 20, 1980.

This invention relates to a novel 2-oxoimidazolidine derivative and a process for preparing same. More particularly, it relates to a compound of the general formula:

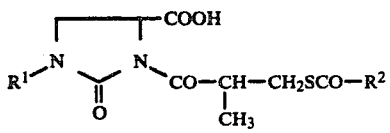

wherein $R^1$ is lower alkyl or phenyl-lower alkyl and $R^2$ is lower alkyl or phenyl, or a pharmaceutically acceptable salt thereof.

It is known that the enzyme renin splits a leucyl-leucine bond of angiotensinogen to produce angiotensin I. Angiotensin I is converted by angiotensin-converting enzyme (ACE) to angiotensin II which is an active pressor substance and causative of various forms of hypertension in mammalian species. It is also known that ACE decomposes and inactivates bradykinin, thereby serving to increase blood pressure. Thus, intensive studies have been made in recent years to investigate ACE-inhibitors because such inhibitors may be used for the treatment of patients with high blood pressure.

As a result of various investigations, we have now found that the novel 2-oxoimidazolidine derivative (I) of the present invention shows potent inhibitory activity against ACE and is useful as a diagnostic or therapeutic agent for hypertension. For example, when the ACE-inhibitory activity was estimated in vivo by the use of rats which were administered angiotensin I intravenously, (4S)-1-methyl-3-[(2S)-3-benzoylthio-2-methylpropionyl]-2-oxo-imidazolidine-4-carboxylic acid at a dose of 1.0 mg/kg showed about 90% inhibition of ACE-activity. Further, when a test compound was administered orally to spontaneously hypertensive rats, (4S)-1-benzyl-3-[(2S)-3-benzoylthio-2-methylpropionyl]-2-oxo-imidazolidine-4-carboxylic acid at a dose of 50 mg/kg showed a decrease of about 44 mmHg in blood pressure and said hypotensive activity of the test compound lasted for more than 6 hours. In addition, the 2-oxoimidazolidine derivative (I) of the invention shows a preventive effect upon aggregation of blood platelets and the toxicity thereof is also low. For example, when (4S)-1-benzyl-3-[(2S)-3-benzoylthio-2-methylpropionyl]-2-oxo-imidazolidine-4-carboxylic acid was administered orally to mice at a dose of 3 g/kg, no mouse died within 7 days after said administration.

Representative examples of the 2-oxoimidazolidine derivative of the invention include those of the formula (I) in which $R^1$ is lower alkyl such as methyl, ethyl, n-propyl, isopropyl, n-butyl or isobutyl, or phenyl-lower alkyl such as benzyl, and $R^2$ is lower alkyl such as methyl, ethyl, n-propyl, isopropyl, n-butyl or isobutyl, or phenyl. Among them, a preferred subgenus includes the compound of the formula (I) in which $R^1$ is alkyl of one to four carbon atoms or benzyl, and $R^2$ is methyl or phenyl. Another preferred subgenus is the compound of the formula (I) in which $R^1$ is methyl, ethyl or benzyl, and $R^2$ is methyl or phenyl. More preferred subgenus is the compound of the formula (I) in which $R^1$ is methyl, ethyl, or benzyl, and $R^2$ is phenyl. Further preferred 2-oxoimidazolidine derivative of the invention is (4S)-1-methyl, ethyl or benzyl-3-[(2S)-3-benzoylthio-2-methylpropionyl]-2-oxo-imidazolidine-4-carboxylic acid.

According to the present invention, the 2-oxoimidazolidine derivative (I) can be prepared by condensing a compound of the formula:

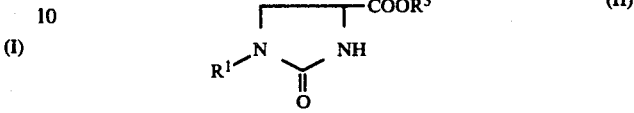

wherein $R^3$ is a protecting group and $R^1$ is the same as defined above, with a propionyl halide of the formula:

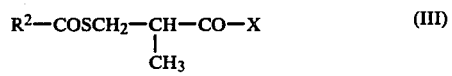

wherein X is halogen atom and $R^2$ is the same as defined above, to give a compound of the formula:

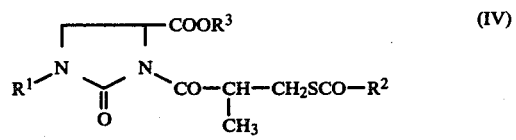

wherein $R^1$, $R^2$ and $R^3$ are the same as defined above, and then removing the protecting group ($R^3$) from the compound (IV).

The condensation reaction of the compounds (II) and (III) can be conducted in the presence of an acid acceptor in an inert solvent. Preferred examples of the acid acceptor include sodium hydride, potassium tert.-butoxide and the like, and tetrahydrofuran, dioxane and dimethoxyethane are suitable as the inert solvent. The reaction proceeds smoothly at a temperature between −10° C. and 80° C., especially at a temperature of 20° C. to 30° C. If the starting compound(s) (II) and/or (III) each one of which involves an asymmetric carbon atom within its molecule is or are used in the racemic form, the compound (IV) is obtained as a mixture of two diastereomers or two optical isomers. If required, however, such two optical isomers or diastereomers can be readily separated into each optical isomers or diastereomers in a conventional manner, for example, by purification of the compound (IV) on a silica gel column.

The removal of the protecting group ($R^3$) from the compound (IV) can be easily accomplished. For example, said removal of the protecting group is preferably carried out by contacting the compound (IV) with an acid in an inert solvent. Suitable examples of the acid include trifluoro-acetic acid, hydrogen fluoride, hydrogen bromide, hydrogen chloride and the like. Dioxane, tetrahydrofuran and ethyl acetate are suitable as the inert solvent. When trifluoroacetic acid is employed as the acid, however, it is not always necessary to use the solvent because said acid serves as the solvent. The reaction proceeds smoothly at a temperature between 0° C. and 50° C., especially at a temperature of 20° C. to 30° C.

The 2-oxoimidazolidine derivative (I) of the present invention involves two asymmetric carbon atoms therein. However, since all of the above-mentioned reactions of the invention can be carried out without racemization, said 2-oxoimidazolidine derivative (I) can be readily obtained in the form of any desired optically active isomer by the use of the corresponding optically active isomer of each one of the compounds (II) and (III) as the starting materials.

The 2-oxoimidazolidine derivative (I) thus obtained shows potent and long-lasting ACE-inhibitory activity and is useful as a hypotensive agent. It can be used for pharmaceutical use either as the free acid or a salt thereof. Pharmaceutically acceptable salts of the 2-oxoimidazolidine derivative (I) include, for example, inorganic salts such as sodium, potassium, calcium and magnesium salts, organic salts such as lysine and arginine salts, and the like. A daily dose of the 2-oxoimidazolidine derivative (I) or a salt thereof may be about 0.6 mg to about 60 mg, especially about one mg to about 20 mg, per kg of body weight. Further, the 2-oxoimidazolidine derivative (I) or its salt may be used in the form of a pharmaceutical preparation containing the same derivative in conjunction or admixture with a pharmaceutical excipient suitable for oral or parenteral administration. Suitable excipients include, for example, starch, lactose, glucose, potassium phosphate, corn starch, arabic gum, stearic acid and other known medicinal excipients. The pharmaceutical preparation may be in solid form such as tablets, powder, pills or capsules; or in liquid form such as solutions, suspensions or emulsions. They may be sterilized and/or may further contain auxiliaries such as stabilizing, wetting or emulsifying agents.

Concomitantly, the starting compound (II) of the invention is a novel compound and can be prepared, for example, according to the method shown in the following reaction scheme:

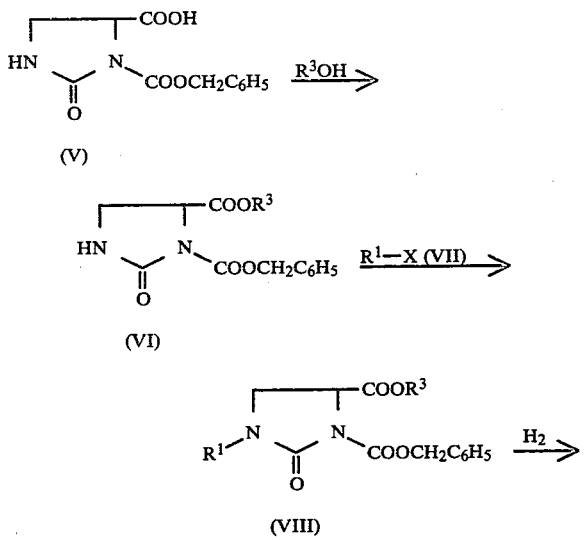

wherein $R^1$, $R^3$ and X are the same as defined above. Since all these reactions proceed without racemization, the compound (II) is readily obtained in an optically active form by the use of the corresponding optically active isomer of the compound (V). On the other hand, an optically active isomer of the propionyl halide(III) is obtained by converting the corresponding propionic acid (racemic form) of the formula:

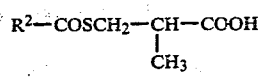

wherein $R^2$ is the same as defined above, into an optically active phenylalanine amide salt thereof, separating the resultant diastereisomers into each enantiomers thereof by fractional crystallization, and then reacting the thus-obtained optically active propionic acid with thionyl chloride in a manner known per se.

Practical and presently preferred embodiments of the present invention are illustratively shown in the following Examples. Throughout the specification and claims, the term "lower alkyl" should be interpreted as referring to alkyl of one to four carbon atoms.

EXAMPLE 1

(1) 5.1 g of (4S)-3-benzyloxycarbonyl-2-oxo-imidazolidine-4-carboxylic acid (Liebich's Annalen der Chemie 529 (1937), page (1) are dissolved in 20 ml of pyridine, and 50 ml of tert.-butanol are added thereto. The solution is cooled to a temperature below $-5°$ C., and 3.5 g of phosphorus oxychloride are added dropwise thereto. The mixture is stirred at the same temperature for about 30 minutes and then at room temperature for 3 hours. The reaction mixture is poured into 200 ml of ice-water, and extracted with ethyl acetate. The extract is washed with 1% hydrochloric acid, an aqueous sodium bicarbonate solution and water, successively. Then, the extract is dried and evaporated to remove solvent. The residue obtained is crystallized with a mixture of ether and n-hexane. 5.5 g of tert.-butyl (4S)-3-benzyloxycarbonyl-2-oxo-imidazolidine-4-carboxylate are obtained as colorless crystals. Yield: 89.0% M.P. 138°–139° C.

(2) 9.6 g of tert.-butyl (4S)-3-benzyloxycarbonyl-2-oxo-imidazolidine-4-carboxylate are dissolved in 200 ml of dimethylformamide, and 14.0 g of silver oxide are added thereto. 42.6 g of methyl iodide are added to the mixture at room temperature under stirring, and the mixture is further stirred for 2 days in the dark. The reaction mixture is filtered to remove insoluble materials, and the filtrate is condensed under reduced pressure. The residue obtained is dissolved in ethyl acetate. Then, the ethyl acetate solution is washed with water, dried and condensed under reduced pressure. The residue thus obtained is washed with n-hexane. 8.45 g of tert.-butyl (4S)-1-methyl-3-benzyloxycarbonyl-2-oxo-imidazolidine-4-carboxylate are thereby obtained as colorless crystals. Yield: 84.3% M.p. 102°–103° C.

(3) 8.5 g of tert.-butyl (4S)-1-methyl-3-benzyloxycarbonyl-2-oxo-imidazolidine-4-carboxylate are dissolved in 200 ml of methanol, and 0.1 g of palladium-black is added thereto. The mixture is shaken at room temperature in hydrogen gas atmosphere under atmospheric pressure. After the reaction the catalyst is removed by filtration, and the filtrate is condensed under reduced pressure. The residue obtained is washed with n-hexane. 5.0 g of tert.-butyl (4S)-1-methyl-2-oxo-imidazolidine-4-carboxylate are obtained as colorless crystals. Yield: 98.2% M.p. 135°–136° C.

(4) 3.0 g of tert.-butyl (4S)-1-methyl-2-oxo-imidazolidine-4-carboxylate are dissolved in 30 ml of tetrahydrofuran, and 0.7 g of sodium hydride (62% oil dispersion) is added thereto under ice-cooling and stirring. A solution of 3-benzoylthio-2-methylpropionyl chloride (prepared by heating a mixture of 4.5 g of 3-benzoylthio-2- methylpropionic acid and 20 ml of thionyl chloride at 50° C. for 3 hours and then evaporating excess thionyl chloride under reduced pressure) in 10 ml of tetrahydrofuran is added dropwise to the mixture at the same temperature. After the mixture is stirred at room temperature overnight, the reaction mixture is condensed under reduced pressure. The residue is dissolved in ethyl acetate, and said ethyl acetate solution is washed with water, 1% hydrochloride acid and an aqueous sodium bicarbonate solution, successively. Then, said solution is dried and evaporated to remove solvent. The oily residue thus obtained is purified by silica gel column chromatography (Solvent, toluene-ethyl acetate (9:1)), whereby tert.-butyl (4S)-1-methyl-3-[(2S)-3-benzoylthio-2-methylpropionyl]-2-oxo-imidazolidine-4-carboxylate(hereinafter referred to as "α-isomer") and then tert.-butyl (4S)-1-methyl-3-[(2R)-3-benzoylthio-2-methylpropionyl]-2-oxo-imidazolidine-4-carboxylate (hereinafter referred to as "β-isomer") are eluted into the eluates, successively.

α-isomer:
  Colorless crystals, Yield: 1.4 g(23.0%)
  M.p. 128° C.
  IR$\gamma_{max}$.$^{Nujol}$: 1750, 1735, 1730, 1660.

β-isomer:
  Colorless syrup, Yield: 1.3 g (21.3%)
  IR$\gamma_{max}$.$^{film}$: 1775, 1740, 1675, 1665.

(5) A mixture of 1.0 g of the α-isomer obtained in paragraph (4) and 5 ml of trifluoroacetic acid is stirred at room temperature for one hour. The reaction mixture is condensed under reduced pressure, and the residue is washed with n-hexane, 0.85 g of (4S)-1-methyl-3-[(2S)-3-benzoylthio--b 2-methylpropionyl]-2-oxo-imidazolidine-4-carboxylic acid is obtained as colorless syrup. Yield: 98.6%

Dicyclohexylamine salt:
  M.p. 200° C. (recrystallized from isopropanol)
  $[\alpha]_D^{28}$ −95.4° (c=0.5, methanol)

L-lysine salt:
  M.p. 124°–128° C.(decomp.)

(6) 1.0 g of the β-isomer obtained in paragraph (4) and 5 ml of trifluoroacetic acid are treated in the same manner as described in paragraph (5). 0.72 g of (4S)-1-methyl-3-[(2R)-3-benzoylthio-2-methylpropionyl]-2-oxo-imidazolidine-4-carboxylic acid is thereby obtained as colorless crystals. Yield: 83.5% M.p. 162° C.(recrystallized from a mixture of ethyl acetate and n-hexane). $[\alpha]_D^{28}$ 23.2°(c=0.5, methanol)

EXAMPLE 2

(1) 61.5 g of 3-benzoylthio-2-methylpropionic acid and 45.0 g of L-phenylalanine amide are dissolved in 1.2 liters of ethyl acetate under heating. After cooling the mixture at room temperature, crystalline precipitates are collected by filtration, dried and then recrystallized from ethyl acetate. 31 g of (2S)-3-benzoylthio-2-methylpropionic acid L-phenylalanine amide salt are thereby obtaineds colorless crystals. M.p. 124°–125° C. $[\alpha]_D^{21}$ −59.4°(c=0.5, chloroform)

28.0 g of said L-phenylalanine amide salt are dissolved in 200 ml of 5% hydrochloric acid, and the solution is extracted with ether. The extract is dried and condensed to dryness under reduced pressure. 15.0 g of (2S)-3-benzoylthio-2-methylpropionic acid are obtained as colorless crystals. M.p. 69°–71° C. $[\alpha]_D^{21}$ −41.7°(c=1, methanol)

(2) 3.0 g of tert.-butyl (4S)-1-methyl-2-oxo-imidazolidine-4-carboxylate are dissolved in 20 ml of tetrahydrofuran. 1.7 g of potassium tert.-butoxide are added to the solution under cooling at about −30° C. and stirring, and the mixture is further stirred at the same temperature for 10 minutes. A solution of (2S)-3-benzoylthio-2-methylpropionyl chloride (prepared by heating the mixture of 3.4 g of (2S)-3-benzoylthio-2-methylpropionic acid and 10 ml of thionyl chloride at 50°–60° C. for 2 hours and then evaporating excess thionyl chloride under reduced pressure) in 10 ml of tetrahydrofuran is added dropwise to the mixture under ice-cooling and stirring. Then, said mixture is further stirred at room temperature overnight. After the reaction, the mixture is condensed under reduced pressure, and the residue is dissolved in ethyl acetate. The ethyl acetate solution is washed with water and an aquous sodium bicarbonate solution, dried and then evaporated to remove solvent. The oily residue thus obtained is purified by silica gel column chromatography (Solvent, toluene-ethyl acetate(20:1)). 4.5 g of tert-butyl (4S)-1-methyl-3-[(2S)-3-benzoylthio-2-methylpropionyl]-2-oxo-imidazolidine-4-carboxylate are obtained as colorless crystals. Yield: 73.9% M.p. 128° C.

(3) 15 ml of trifluoroacetic acid are added to 4.0 g of tert.-butyl (4S)-1-methyl-3-[(2S)-3-benzoylthio-2-methylpropionyl]-2-oxo-imidazolidine-4-carboxylate, and the mixture is stirred at room temperature for 2 hours. The reaction mixture is condensed under reduced pressure. Toluene is added to the residue, and said mixture is again condensed under reduced pressure. The residue thus obtained is recrystallized from a mixture of ethyl acetate and n-hexane. 3.2 g of (4S)-1-methyl-3-[(2S)-3-benzoylthio-2-methylpropionyl]-2-oxo-imidazolidine-4-carboxylic acid is thereby obtained as colorless syrup. The physico-chemical properties of this product are identical with those of the sample obtained in Example 1-(5).

EXAMPLE 3

(1) 1.3 g of tert.-butyl (4S)-1-methyl-2-oxo-imidazolidine-4-carboxylate are dissolved in 15 ml of tetrahydrofuran, and 0.35 g of sodium hydride (62% oil dispersion) is added thereto under ice-cooling and stirring. A solution of (2S)-3-acetylthio-2-methylpropionyl chloride (prepared by heating a mixture of 1.5 g of (2S)-3-acetylthio-2-methylpropionic acid and 6 ml of thionyl chloride at 50° C. for 3 hours and then evaporting excess thionyl chloride under reduced pressure) in 5 ml of tetrahydrofuran is added dropwise to the mixture. Then, the mixture is treated in the same manner as described in Example 1-(4). 1.0 g of tert.-butyl (4S)-1-methyl-3-[(2S)-3-acetylthio-2-methylpropionyl]-2-oxoimidazolidine-4-carboxylate is obtained as colorless crystals.
Yield: 44.7%
M.p. 104°–104.5° C.
IR$\gamma_{max}$.$^{Nujol}$(cm$^1$): 1755, 1745, 1700, 1670.

(2) A mixture of 0.72 g of tert.-butyl (4S)-1-methyl-3-[(2S)-3-acetylthio-2-methylpropionyl]-2-oxo-imidazolidine-4-carboxylate and 3.5 ml of trifluoroacetic acid is stirred at room temperature for one hour. Then, the reaction mixture is treated in the same manner as described in Example 1-(5). 0.6 g of (4S)-1-methyl-3-[(2S)-3-acetylthio-2-methylpropionyl]-2-oxo-imidazolidine-4-carboxylic acid is obtained as colorless syrup. Yield: quantitative.
IR$\gamma_{max}$.$^{film}$(cm$^1$): 1730(broad), 1685(broad)
$[\alpha]_D^{28}$ −151.0°(c=0.5, methanol)

EXAMPLE 4

(1) 9.6 g of tert.-butyl (4S)-3-benzyloxycarbonyl-2-oxo-imidazolidine-4-carboxylate, 14.0 g of silver oxide, 46.8 g of ethyl iodide and 200 ml of dimethylformamide are treated in the same manner as described in Example 1-(2). 6.2 g of tert.-butyl (4S)-1-ethyl-3-benzyloxycarbonyl-2-oxo-imidazolidine-4-carboxylate are obtained as colorless crystals.

Yield: 59.4% M.p. 97° C.

(2) 4.2 g of tert.-butyl (4S)-1-ethyl-3-benzyloxycarbonyl-2-oxo-imidazolidine-4-carboxylate, 0.1 g of palladium-black and 100 ml of methanol are treated in the same manner as described in Example 1-(3). 2.5 g of tert.-butyl (4S)-1-ethyl-2-oxo-imidazolidine-4-carboxylate are thereby obtained as colorless crystals. Yield: 96.9% M.p. 86°-87° C.

(3) 2.5 g of tert.-butyl (4S)-1-ethyl-2-oxo-imidazolidine-4-carboxylate are dissolved in 30 ml of tetrahydrofuran, and 0.55 g of sodium hydride (62% oil dispersion) is added thereto under ice-cooling and stirring. A solution of 3-benzoylthio-2-methylpropionyl chloride (prepared from 3.2 g of 3-benzoylthio-2-methylpropionic acid and 15 ml of thionyl chloride) in 10 ml of tetrahydrofuran is added dropwise to the mixture, and then said mixture is treated in the same manner as described in Example 1-(4). The oily residue obtained is purified by silica gel column chromatography, whereby tert.butyl (4S)-1-ethyl-3-[(2S)-3-benzoylthio-2-methylpropionyl]-2-oxo-imidazolidine-4-carboxylate (hereinafter referred to as "α-isomer") and then tert.-butyl (4S)-1-ethyl-3-[(2R)-3-benzoylthio-2-methylpropionyl]-2-oxo-imidazolidine-4-carboxylate (hereinafter referred to as "β-isomer") are eluted into the eluates, successively.

α-isomer:
Colorless crystals, Yield: 1.2 g (24.5%),
M.p. 92°-93° C.
IR$\gamma_{max}^{Nujol}$(cm$^{-1}$): 1730(broad), 1665.

β-isomer:
Colorless syrup, Yield: 1.4 g (28.5%),
IR$\gamma_{max}^{film}$(cm$^{-1}$): 1730(broad), 1670(broad).

(4) 0.9 g of the α-isomer obtained in paragraph (3) and 5 ml of tetrafluoroacetic acid are treated in the same manner as described in Example 1-(5). 0.76 g of (4S)-1-ethyl-3-[(2S)-3-benzoylthio-2-methylpropionyl]-2-oxo-imidazolidine-4-carboxylic acid is obtained as colorless crystals.

Yield: 97.4%
M.p. 148° C.(recrystallized from a mixture of ethyl acetate and n-hexane).
IR$\gamma_{max}^{Nujol}$(cm$^{-1}$): 1740, 1690, 1675, 1660.
$[\alpha]_D^{28}$ −126.8°(c=0.5, methanol).

(5) 0.9 g of the β-isomer obtained in paragraph (3) and 5 ml of trifluoroacetic acid are treated in the same manner as described in Example 1-(5). 0.65 g of (4S)-1-ethyl-3-[(2R)-3-benzoylthio-2-methylpropionyl]-2-oxo-imidazolidine-4-carboxylic acid is obtained as colorless crystals. Yield: 83.3%
M.p. 139°-141° C. (recrystallized from a mixture of ethyl acetate and n-hexane)
IR$\gamma_{max}^{Nujol}$(cm$^{-1}$): 1760, 1730, 1670,1640.
$[\alpha]_D^{28}$ +14.3°(c=0.28, methanol)

EXAMPLE 5

(1) 3.0 g of tert.-butyl (4S)-1-ethyl-2-oxo-imidazolidine-4-carboxylate, 1.6 g of potassium tert.-butoxide, (2S)-3-benzoylthio-2-methylpropionyl chloride (prepared from 3.2 g of (2S)-3-benzoylthio-2-methylpropionic acid and 10 ml of thionyl chloride) and 40 ml of tetrahydrofuran are treated in the same manner as described in Example 2-(2). Then, the oily residue obtained is purified by silica gel chromatography (Solvent, toluene-ethyl acetate(20:1)). 4.2 g of tert.-butyl (4S)-1-ethyl-3-[(2S)-3-benzoylthio-2-methylpropionyl]-2-oxo-imidazolidine-4-carboxylate are obtained as colorless crystals.

Yield: 71.3% M.p. 92°-93° C.

(2) 4.0 g of tert.-butyl (4S)-1-ethyl-3-[(2S)-3-benzoylthio-2-methylpropionyl]-2-oxo-imidazolidine-4-carboxylate and 15 ml of trifluoroacetic acid are treated in the same manner as described in Example 2-(3). 3.3 g of (4S)-1-ethyl-3-[(2S)-3-benzoylthio-2-methylpropionyl]-2-oxo-imidazolidine-4-carboxylic acid are obtained as colorless crystals. Yield: 95.2% The physico-chemical properties of this product are identical with those of the sample obtained in Example 4-(4).

EXAMPLE 6

(1) 6.4 g of tert.-butyl (4S)-3-benzyloxycarbonyl-2-oxo-imidazolidine-4-carboxylate, 8.6 g of silver oxide, 18.4 g of n-butyl iodide and 100 ml of dimethylformamide are treated in the same manner as described in Example 1-(2). 6.7 g of tert.-butyl (4S)-1-n-butyl-3-benzyloxycarbonyl-2-oxo-imidazolidine-4-carboxylate are obtained as colorless syrup.

Yield: 89.1%

(2) 6.7 g of tert.-butyl (4S)-1-n-butyl-3-benzyloxycarbonyl-2-oxo-imidazolidine-4-carboxylate, 0.1 g of palladium-black and 200 ml of methanol are treated in the same manner as described in Example 1-(3). 3.8 g of tert.-butyl (4S)-1-n-butyl-2-oxo-imidazolidine-4-carboxylate are obtained as colorless syrup. Yield: 88.1%
IR$\gamma_{max}^{film}$(cm$^{-1}$): 3250, 1720(broad)

(3) 3.0 g of tert.-butyl (4S)-1-n-butyl-2-oxo-imidazolidine-4-carboxylate, 0.53 g of sodium hydride (62% oil dispersion), 3-benzoylthio-2-methylpropionyl chloride (prepared from 3.4 g of 3-benzoylthio-2-methylpropionic acid and 15 ml of thionyl chloride) and 20 ml of tetrahydrofuran are treated in the same manners as described in Example 1-(4). The oily residue obtained is purified by silica gel column chromatography, whereby tert.-butyl (4S)-1-n-butyl-3-[(2S)-3-benzoylthio-2-methylpropionyl]-2-oxo-imidazolidine-4-carboxylate (hereinafter referred to as "α-isomer") and then tert.-butyl (4S)-1-n-butyl-3-[(2R)-3-benzoylthio-2-methylpropionyl]-2-oxo-imidazolidine-4-carboxylate (hereinafter referred to as "β-isomer") are eluted into the eluates, successively.

α-isomer:
Colorless syrup, Yield: 1.2 g (21.6%)
IR$\gamma_{max}^{film}$(cm$^{-1}$): 1740(broad), 1670(broad).

β-isomer
Colorless syrup, Yield: 1.2 g (21.6%),
IR$\gamma_{max}^{film}$(cm$^{-1}$): 1740(broad), 1670(broad).

(4) 1.0 g of the α-isomer obtained in paragraph(3) and 5 ml of trifluoroacetic acid are treated in the same manner as described in Example 1-(5). 0.7 g of (4S)-1-n-butyl-3-[(2S)-3-benzoylthio-2-methylpropionyl]-2-oxo-imidazolidine-4-carboxylic acid is obtained as colorless crystals.

Yield: 80%
M.p. 119° C. (recrystallized from a mixture of ethyl acetate and n-hexane).
IR$\gamma_{max}^{Nujol}$(cm$^{-1}$): 1740, 1690(broad), 1660
$[\alpha]_D^{25}$ −102.8°(c=0.5, methanol).

(5) 1.0 g of the β-isomer obtained in paragraph (3) and 5 ml of trifluoroacetic acid are treated in the same manner as described in Example 1-(5). 0.75 g of (4S)-1-n-butyl-3-[(2R)-3-benzoylthio-2-methylpropionyl]-2-oxo-imidazolidine-4-carboxylic acid is obtained as colorless syrup. Yield: 85.7%
Dicyclohexylamine salt:
M.p. 125°–127° C.
$[\alpha]_D^{25}$ −1.4°(c=1.0, methanol)

EXAMPLE 7

(1) 3.0 g of tert.-butyl (4S)-1-n-butyl-2-oxo-imidazolidine-4-carboxylate, 1.4 g of potassium tert.-butoxide, (2S)-3-benzoylthio-2-methylpropionyl chloride (prepared from 2.8 g of (2S)-3-benzoylthio-2-methylpropionic acid and 10 ml of thionyl chloride) and 40 ml of tetrahydrofuran are treated in the same manner as described in Example 2-(2). Then, the oily residue obtained is purified by silica gel chromatography (Solvent, toluene-ethyl acetate (20:1)). 3.8 g of tert.-butyl (4S)-1-n-butyl-3-[(2S)-3-benzoylthio-2-methylpropionyl]-2-oxo-imidazolidine-4-carboxylate are obtained as colorless syrup.
Yield: 68.4%

(2) 3.5 g of tert.-butyl (4S)-1-n-butyl-3-[(2S)-3-benzoylthio-2-methylpropionyl]-2-oxo-imidazolidine-4-carboxylate and 15 ml of trifluoroacetic acid are treated in the same manner as described in Example 2-(3). 2.8 g of (4S)-1-n-butyl-3-[(2S)-3-benzoylthio-2-methylpropionyl]-2-oxo-imidazolidine-4-carboxylic acid are obtained as colorless crystals. Yield: 91.4% The physicochemical properties of this product are identical with those of the sample obtained in Example 6-(4).

EXAMPLE 8

(1) A mixture of 9.6 g of tert.-butyl (4S)-3-benzyloxycarbonyl-2-oxo-imidazolidine-4-carboxylate, 8.3 g of potassium carbonate, 20 g of benzyl bromide and 200 ml of acetone is stirred at room temperature for 3 days. Then, the reaction mixture is treated in the same manner as described in Example 1-(2). 9.3 g of tert.-butyl (4S)-1-benzyl-3-benzyloxycarbonyl-2-oxo-imidazolidine-4-carboxylate are obtained as colorless syrup. Yield: 75.6%
IR$\gamma_{max}^{film}$(cm$^{-1}$): 1790, 1740, 1715.

(2) 7.4 g of tert.-butyl (4S)-1-benzyl-3-benzyloxycarbonyl-2-oxo-imidazolidine-4-carboxylate, 0.1 g of palladium-black and 200 ml of methanol are treated in the same manner as described in Example 1-(3). 4.7 g of tert.-butyl(4S)-1-benzyl-2-oxo-imidazolidine-4-carboxylate are obtained as colorless crystals. Yield: 94.3%
M.p. 96°–98° C.
IR$\gamma_{max}^{KBr}$(cm$^{-1}$): 3250, 1730, 1705.

(3) 4.9 g of tert.-butyl (4S)-1-benzyl-2-oxo-imidazolidine-4-carboxylate, 0.8 g of sodium hydride (62% oil dispersion), 3-benzoylthio-2-methylpropionyl chloride (prepared from 5.2 g of 3-benzoylthio-2-methylpropionic acid and 20 ml of thionyl chloride) and 40 ml of tetrahydrofuran are treated in the same manner as described in Example 1-(4). The oily residue obtained is purified by silica gel column chromatography, whereby tert.-butyl (4S)-1-benzyl-3-[(2S)-3-benzoylthio-2-methylpropionyl]-2-oxo-imidazolidine-4-carboxylate (hereinafter referred to as "α-isomer") and then tert.-butyl (4S)-1-benzyl-3-[(2R)-3-benzoylthio-2-methylpropionyl]-2-oxo-imidazolidine-4-carboxylate (hereinafter referred to as "β-isomer") are eluted into the eluates, successively.
α-isomer:
Colorless syrup, Yield: 2.1 g (24.5%).
IR$\gamma_{max}^{film}$(cm$^{-1}$): 1770(broad), 1735,
β-isomer:
Colorless syrup, Yield: 2.0 g (23.4%).
IR$\gamma_{max}^{film}$(cm$^{-1}$): 1770(broad), 1735.

(4) 1.0 g of the α-isomer obtained in paragraph (3) and 5 ml of trifluoroacetic acid are treated in the same manner as described in Example 1-(5). 0.8 g of (4S)-1-benzyl-3-[(2S)-3-benzoylthio-2-methylpropionyl]-2-oxo-imidazolidine-4-carboxylic acid is obtained as colorless crystals.
Yield: 90.5%
M.p. 145° C. (recrystallized from a mixture of ethyl acetate and n-hexane).
IR$\gamma_{max}^{Nujol}$(cm$^{-1}$): 1740, 1705, 1690, 1665.
$[\alpha]_D^{28}$ −101.2°(c=0.5, methanol).

(5) 1.0 g of the β-isomer obtained in paragraph (3) and 5 ml of trifluoroacetic acid are treated in the same manner as described in Example 1-(5). 0.88 g of (4S)-1-benzyl-3-[(2R)-3-benzoylthio-2-methylpropionyl]-2-oxo-imidazolidine-4-carboxylic acid is obtained as colorless syrup. Yield: quantitative
Dicyclohexylamine salt:
M.p. 165°–166° C. (recrystallized from ethyl acetate).
$[\alpha]_D^{28}$ +8.0(c=0.5, methanol).
L-Lysine salt:
M.p. 150°–155° C.(decomp.).

EXAMPLE 9

(1) 27.6 g of tert.-butyl (4S)-1-benzyl-2-oxo-imidazolidine-4-carboxylate, 11.2 g of potassium tert.-butoxide, (2S)-3-benzoylthio-2-methylpropionyl chloride (prepared from 22.4 g of (2S)-3-benzoylthio-2-methylpropionic acid and 25 ml of thionyl chloride) and 200 ml of tetrahydrofuran are treated in the same manner as described in Example 2-(2). Then, the oily residue obtained is purified by silica gel chromatography (Solvent, toluene-ethyl acetate(20:1)) and triturated with n-hexane. 34.1 g of tert.-butyl (4S)-1-benzyl-3-[(2S)-3-benzoylthio-2-methylpropionyl]-2-oxo-imidazolidine-4-carboxylate are obtained as colorless crystals. Yield: 70.7%
M.p. 104°–106° C.
$[\alpha]_D^{18}$ −88.5°(c=1.0, methanol)

(2) 30 g of tert.-butyl (4S)-1-benzyl-3-[(2S)-3-benzoylthio-2-methylpropionyl]-2-oxo-imidazolidine-4-carboxylate and 120 ml of trifluoroacetic acid are treated in the same manner as described in Example 2-(3). 24.1 g of (4S)-1-benzyl-3-[(2S)-3-benzoylthio-2-methylpropionyl]-2-oxo-imidazolidine-4-carboxylic acid are obtained as colorless crystals. Yield: 90.9% The physicochemical properties of this product are identical with those of the sample obtained in Example 8-(4).

EXPERIMENT 1

ACE-inhibitory activity in vivo:
Normotensive rats were anesthetized with urethane (1.5 g/kg, s.c.), and agiotensin I (75~300 ng/kg) was injected into the femoral vein of the rates. The pressor response to angiotensin I was measured with a pressure transducer connected to the carotid artery. Then, a test compound was administered orally thereto at a dose of 1.0 mg/kg, and angiotensin I (300 ng/kg) was further injected intravenously at intervals. The ACE-inhibitory activity of the test compound was estimated from the pressor responses to angiotensin I which were obtained before and after oral administration of the test compound. The results are shown in the following Table 1.

TABLE 1

$$R^1-N\underset{\underset{O}{\|}}{\overset{(S)}{\overset{|}{\frown}}}N-CO-\overset{(S)}{\underset{CH_3}{\overset{|}{CH}}}-CH_2-S-COR^2$$

| Test compounds | | ACE-inhibitory activity (%)* | Duration of action (minutes) |
|---|---|---|---|
| $R^1$ | $R^2$ | | |
| $CH_3$ | $C_6H_5$ | 88 | >120 |
| $CH_3$ | $CH_3$ | 67 | >120 |
| $C_2H_5$ | $C_6H_5$ | 84 | >120 |
| $C_6H_5CH_2$ | $C_6H_5$ | 76 | >120 |

Note:
(S) means that the carbon atom has S-configuration
*percentage inhibition of ACE-activity in vivo.

EXPERIMENT 2

Hypotensive activity in SHR:

A test compound suspended in an aqueous carboxymethylcellulose solution was administered orally to spontaneously hypertensive rats (SHR) fasted overnight. The systolic blood pressure of the rats was measured by the tail plethysmographic technique (The Journal of Laboratory and Clicical Medicine 78 (1971), page 957). The hypotensive activity of the test compound was estimated from the decreased level of blood pressure. The results are shown in the following Table 2.

TABLE 2

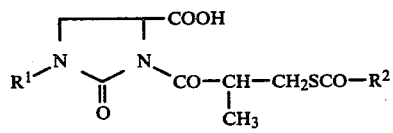

| Test compounds | | Dose (mg/kg) | Decrease in blood pressure (−ΔmmHg) | Duration of action (hours) |
|---|---|---|---|---|
| $R^1$ | $R^2$ | | | |
| $CH_3$ | $CH_3$ | 50 | 37 | >6 |
| $C_6H_5CH_2$ | $C_6H_5$ | 50 | 44 | >6 |

Note:
(S) means that the carbon atom has S-configuration.

What we claim is:
1. A 2-oxoimidazolidine derivative of the formula:

$$R^1-N\underset{\underset{O}{\|}}{\overset{\overset{|}{\frown}COOH}{\frown}}N-CO-\underset{CH_3}{\overset{|}{CH}}-CH_2SCO-R^2$$

wherein $R^1$ is methyl, ethyl or benzyl and $R^2$ is phenyl, or a pharmaceutically acceptable salt thereof.

2. A (4S)-1-substituted-3-[(2S)-4-acylthio-2-methylpropionyl]-2-oxo-imidazolidine-4-carboxylic acid of the formula:

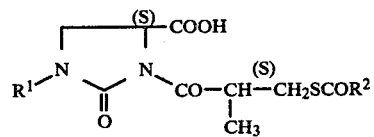

wherein $R^1$ is methyl, ethyl or benzyl and $R^2$ is phenyl, or a pharmaceutically acceptable salt thereof.

* * * * *